United States Patent
Jonczyk et al.

(10) Patent No.: US 6,822,074 B1
(45) Date of Patent: Nov. 23, 2004

(54) PROCESS FOR THE PREPARATION OF CYCLO(ASP-DPHE-NMEVAL-ARG-GLY)

(75) Inventors: Alfred Jonczyk, Darmstadt (DE); Markus Arnold, Neu-Isenburg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/936,230

(22) PCT Filed: Mar. 1, 2000

(86) PCT No.: PCT/EP00/01751

§ 371 (c)(1),
(2), (4) Date: Sep. 12, 2001

(87) PCT Pub. No.: WO00/53627

PCT Pub. Date: Sep. 14, 2000

(30) Foreign Application Priority Data

Mar. 11, 1999 (DE) .......................................... 199 10 727

(51) Int. Cl.[7] .......................... A61K 38/00; A01N 43/00
(52) U.S. Cl. .......................... 530/330; 514/9; 514/183; 530/333; 530/335; 530/338; 530/339
(58) Field of Search ...................... 514/9, 183; 530/330, 530/333, 335, 338, 339

(56) References Cited

U.S. PATENT DOCUMENTS

| 5,767,239 A | 6/1998 | Immer Hansueli et al. |
| 5,849,692 A | 12/1998 | Jonczyk et al. |
| 6,001,961 A | 12/1999 | Jonczyk et al. |
| 6,127,335 A | 10/2000 | Jonczyk et al. |
| 6,169,072 B1 | 1/2001 | Jonczyk et al. |
| 6,566,491 B2 | 5/2003 | Jonczyk et al. |
| 2002/0032306 A1 | 3/2002 | Jonczyk et al. |

FOREIGN PATENT DOCUMENTS

| DE | 01954177 | * | 9/1995 |
| DE | 1038741 A | * | 10/1995 |
| EP | 0 606 881 A | | 7/1994 |
| EP | 0 770 622 A | | 5/1997 |
| WO | WO 97/45447 | * | 12/1997 |
| WO | WO 99 01472 A | | 1/1999 |

* cited by examiner

*Primary Examiner*—Patricia A Patten
(74) *Attorney, Agent, or Firm*—Millen, White, Zelano & Branigan, P.C.

(57) ABSTRACT

Process for the preparation of the cyclic pentapeptide
cyclo(Arg-Gly-Asp-DPhe-NMeVal)
by cyclization of a linear pentapeptide selected from the group consisting of
H-Arg(Pbf)-Gly-Asp(OBzl)-DPhe-NMeVal-OH,
H-Gly-Asp(OBzl)-DPhe-NMeVal-Arg(Pbf)-OH,
H-Asp(OBzl)-DPhe-NMeVal-Arg(Pbf)-Gly-OH,
H-DPhe-NMeVal-Arg(Pbf)-Gly-Asp(OBzl)-OH or
H-NMeVal-Arg(Pbf)-Gly-Asp (OBzl)-DPhe-OH,
subsequent protective group removal and, if appropriate, further conversion into its physiologically acceptable salts.

13 Claims, No Drawings

PROCESS FOR THE PREPARATION OF CYCLO(ASP-DPHE-NMEVAL-ARG-GLY)

This application is a 371 of PCT/EP/00/01751 filed Jan. 3, 2000 which claims benefit of priority to Application number 19910727.0 filed in Germany on Mar. 11, 1999.

The invention relates to a novel process for the preparation of the cyclic pentapeptide cyclo(Arg-Gly-Asp-DPhe-NMeVal).

Cyclic pentapeptides, amongst them also cyclo(Arg-Gly-Asp-DPhe-NMeVal) and its physiologically acceptable salts, are disclosed in EP 0 770 622. The present invention is to be regarded as a selection invention in relation to EP 0 770 622.

Generally, cyclic peptides are obtained by cyclization of a linear precursor molecule under the customary conditions of peptide synthesis. In order that selective linkage of two amino acids or two segments, consisting of a number of amino acids, or alternatively a cyclization of a linear peptide, can be guaranteed, the corresponding functionalities of the amino acids which are not intended to participate in the reaction are to be blocked by appropriate protective groups. Various types of protective groups for amino, carboxyl, hydroxyl, thiol or carboxamide functions, and also for guanidine functions or for the imidazole nitrogen, were therefore developed which, in their combination, make possible a wide possibility of variation with respect to the optimization of the reactions mentioned beforehand. The synthesis of the linear precursor molecules, the linear peptides, can moreover be carried out by means of two methods, on the one hand by means of a solid-phase peptide synthesis, on the other hand in solution. In this case, stepwise couplings of the amino acids or fragment condensations of segments of amino acids are possible. The respective coupling steps can in turn be carried out using different condensation reagents, such as carbodiimides, carbodiimidazole, those of the uronium type such as TBTU, or according to mixed anhydride methods or active ester methods.

The invention was based on the object of developing a novel, improved process for the preparation of cyclo(Arg-Gly-Asp-DPhe-NMeVal), in comparison with the previously known processes.

It was surprisingly found that in the synthesis of the cyclopeptide cyclo(Arg-Gly-Asp-DPhe-NMeVal) by cyclization of a linear precursor molecule, the combination of the protective groups-2,2,4,6,7-pentamethyldihydrobenzofuran-5-sulfonyl (Pbf) for the guanidino group in the side chain of the arginine and benzyl (Bzl) for the carboxyl group in the side chain of the aspartic acid leads to an optimization with respect to the yield.

The invention therefore relates to a process for the preparation of the cyclic pentapeptide cyclo(Arg-Gly-Asp-DPhe-NMeVal)

by cyclization of a linear pentapeptide selected from the group consisting of

H-Arg(Pbf)-Gly-Asp(OBzl)-DPhe-NMeVal-OH,
H-Gly-Asp(OBzl)-DPhe-NMeVal-Arg(Pbf)-OH,
H-Asp(OBzl)-DPhe-NMeVal-Arg(Pbf)-Gly-OH,
H-DPhe-NMeVal-Arg(Pbf)-Gly-Asp(OBzl)-OH or
H-NMeVal-Arg(Pbf)-Gly-Asp(OBzl)-DPhe-OH, subsequent protective group removal and, if appropriate, further conversion into its physiologically acceptable salts.

The invention furthermore relates to a process for the preparation of the cyclic pentapeptide cyclo(Arg-Gly-Asp-DPhe-NMeVal)

as described, characterized in that the linear pentapeptide H-Asp(OBzl)-DPhe-NMeVal-Arg(Pbf)-Gly-OH is cyclized.

The reaction conditions of this cyclization of the linear peptides selected from the group consisting of H-Arg(Pbf)-Gly-Asp(OBzl)-DPhe-NMeVal-OH,
H-Gly-Asp(OBzl)-DPhe-NMeVal-Arg(Pbf)-OH,
H-Asp(OBzl)-DPhe-NMeVal-Arg(Pbf)-Gly-OH,
H-DPhe-NMeVal-Arg(Pbf)-Gly-Asp(OBzl)-OH or
H-NMeVal-Arg(Pbf)-Gly-Asp(OBzl)-DPhe-OH with respect to the choice of the dehydrating agent, the inert solvent and the reaction temperature and the further conversion into its physiologically acceptable salts have already been disclosed in EP 0 770 622.

The benzyl protective group on the side chain of the aspartic acid can be removed under customary conditions (for this cf.: T. W. Greene, P. G. M. Wuts, Protective Groups in Organic Chemistry, $2^{nd}$ Ed., Wiley, New York 1991 or P. J. Kocienski, Protecting Groups, $1^{st}$ Ed., George Thieme Verlag, Stuttgart—New York, 1994, H. Kunz, H. Waldmann in Comprehensive Organic Synthesis, Vol. 6 (Ed. B. M. Trost, I. Fleming, E. Winterfeldt), Pergamon, Oxford. 1991, pp. 631–701), e.g. by treating with hydrogen in the presence of a catalyst (e.g. of a noble metal catalyst such as palladium, expediently on a support such as carbon) Suitable solvents are, for example, alcohols such as methanol or ethanol or amides such as DMF or alternatively mixtures with further inert solvents, such as, for example, mixtures with water. As a rule, the hydrogenolysis is carried out at temperatures between approximately 0 and 100° C. and pressures between approximately 1 and 200 bar, preferably at 20–30° C. and 1–10 bar.

The Pbf protective group, which was introduced into peptide chemistry by L. A. Carpino et al., Tet. Lett. 1993, 34, 7829–7832, is removed, for example, by treating with 95% trifluoroacetic acid (TFA). The Pbf protective group in this case shows a greater lability with respect to TFA than the structurally similar protective groups 4-methoxy-2,3,6-trimethylphenylsulfonyl (Mtr) and 2,2,5,7,8-pentamethylchroman-6-sulfonyl (Pmc), which are also possible as side-chain protective groups with respect to the synthesis of cyclo(Arg-Gly-Asp-DPhe-NMeVal). TEA is preferably used in an excess without addition of a further solvent. TFA can also be employed as a mixture with an inert solvent, such as, for example, the combination TFA/dichloromethane in the ratio 6:4. TFA can furthermore also be employed with an addition of 1–10%, preferably 2%, of water. The reaction temperature for the cleavage is expediently between approximately 0 and approximately 50° C., and the reaction is preferably carried out between 15 and 30° C. (room temperature).

The abbreviations of amino acids listed above and below stand for the radicals of the following amino acids:

| | |
|---|---|
| Asp | Aspartic acid |
| Arg | Arginine |
| Gly | Glycine |
| Phe | Phenylalanine |
| Val | Valine |

Furthermore, above and below the following have the meanings:

| | |
|---|---|
| Boc | tert-Butoxycarbonyl |
| Bzl | Benzyl |
| CHA | Cyclohexylamine |
| D | Characterization of a D-amino acid |
| DCCI | Dicyclohexylcarbodiimide |
| DMAP | Dimethylaminopyridine |
| DMF | Dimethylformamide |
| EDCI | N-Ethyl-N'-(3-dimethylaminopropyl)carbodiimide hydrochloride |
| Et | Ethyl |
| Fmoc | 9-Fluorenylmethoxycarbonyl |
| HOBt | 1-Hydroxybenzotriazole |
| Me | Methyl |
| MTBE | Methyl tert-buty ether |
| Mtr | 4-Methoxy-2,3,6-trimethylphenylsulfonyl |
| NMe | N-methylated α-amino group |
| NMP | N-methylpyrrolidone |
| OtBu | tert-Butyl ester |
| OMe | Methyl ester |
| OEt | Ethyl ester |
| Pbf | 2,2,4,6,7-Pentamethyldihydrobenzofuran-5-sulfonyl |
| Pmc | 2,2,5,7,8-pentamethylchroman-6-sulfonyl |
| POA | Phenoxyacetyl |
| Pr | Propyl |
| Su | Succinimide |
| TBTU | 2-(1H-Benzotriazol-1-yl)-1,1,3,3-tetramethyl-uronium tetrafluoroborate |
| TFA | Trifluoroacetic acid |
| Z | Benzyloxycarbonyl |

It was furthermore surprisingly found that the specific selection of the side-chain protective groups Pbf on Arg and Bzl on Asp even in the synthesis of the linear peptides, which, as mentioned beforehand, are intermediates in the synthesis of cyclo(Arg-Gly-Asp-DPhe-NMeVal), leads to improved yields in the respective synthesis stages. As a result, the yield of cyclo(Arg-Gly-Asp-DPhe-NMeVal) is increased overall and as a result thereof the costs of the synthesis are lowered.

The improvement in yield is achieved in this case both in the solid-phase peptide synthesis and in the synthesis in solution of the linear peptides H-Arg(Pbf)-Gly-Asp-(OBzl)-DPhe-NMeVal-OH, H-Gly-Asp(OBzl)-DPhe-NMeVal-Arg(Pbf)-OH, H-Asp(OBzl)-DPhe-NMeVal-Arg(Pbf)-Gly-OH, H-DPhe-NMeVal-Arg(Pbf)-Gly-Asp(OBzl)-OH or H-NMeVal-Arg(Pbf)-Gly-Asp(OBzl)-DPhe-OH, in particular H-Asp(OBzl)-DPhe-NMeVal-Arg(Pbf)-Gly-OH.

The protected amino acids or amino acid fragments used in the two synthesis methods are customarily prepared by methods of amino acid and peptide synthesis, such as described in the standard works Principles of Peptide Synthesis, ed. M. Bodansky, Springer Verlag Berlin 1984; Houben Weyl, Methoden der organischen Chemie [Methods of Organic Chemistry], 1.c., Volume 15/II, 1974, pages 1 to 806, Georg Thieme Verlag, Stuttgart; Calbiochem/Novabiochem Catalogue and Synthesis Handbook 1999; Synthesis Notes or Peptide Synthesis Protocols, eds. M. W. Pennington and B. M. Dunn in Methods in Molecular Biology, Vol. 35, Humana Press Totowa N.J. 1994, namely under reaction conditions which are known and suitable for the reactions mentioned. Use can also be made in this case of variants which are known, but not mentioned here in greater detail.

The underlying principles of solid-phase peptide synthesis have been laid down by B. F. Gysin and R. B. Merrifield (J. Am. Chem. Soc. 1972, 94, 3102 ff.). The solid-phase synthesis of the linear peptides described beforehand, their removal and purification is carried out as described by A. Jonczyk and J. Meienhofer in Peptides, Proc. 8$^{th}$ Am. Pept. Symp., Eds. V. Hruby and D. H. Rich, Pierce Comp. III, p. 73–77, 1983 or analogously to the techniques described in Angew. Chem. 1992, 104, 375–391.

Particularly preferably, the synthesis of one of the linear peptides, such as described beforehand, takes place convergently by fragment condensation.

The invention therefore furthermore relates to a process for the preparation of the cyclic pentapeptide cyclo(Arg-Gly-Asp-DPhe-NMeVal), characterized in that; the synthesis of the linear peptide H-Asp(OBzl)-DPhe-NMeVal-Arg(Pbf)-Gly-OH is carried out convergently by fragment condensation of a tripeptide $R^1$-Asp(OBzl)-DPhe-NMeVal-OH, where $R^1$ is an amino protective group, with: a dipeptide H-Arg(Pbf)-Gly-$R^2$, where $R^2$ is a carboxyl protective group, and the protective groups $R^1$ and $R^2$ are then removed.

$R^1$, as described beforehand, is an amino protective group. The expression "amino protective group" is generally known and relates to groups which are suitable for protecting (or blocking) an amino group from chemical reactions. Typical groups of this type are, in particular, unsubstituted or substituted acyl, aryl, aralkoxymethyl or aralkyl groups. As the amino protective groups are removed after the desired reaction (or reaction sequence), their nature and size is otherwise uncritical; however, those having 1–20 C atoms are preferred. The expression "acyl group" is to be interpreted in the widest sense in connection with the present process. It includes acyl groups derived from aliphatic, araliphatic, alicyclic, aromatic or heterocyclic carboxylic acids or sulfonic acids and also, in particular, alkoxycarbonyl, alkenyloxycarbonyl, aryloxycarbonyl and especially aralkoxycarbonyl groups. Examples of acyl groups of this type are formyl or alkanoyl such as acetyl, propionyl, butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, Boc, 2-iodoethoxycarbonyl; alkenyloxycarbonyl such as aryloxycarbonyl (Aloc), aralkyloxycarbonyl such as CBZ (synonymous with Z), 4-methoxybenzyloxycarbonyl (MOZ), 4-nitrobenzyloxycarbonyl or 9-fluorenylmethoxycarbonyl (Fmoc); 2-(phenylsulfonyl)ethoxycarbonyl; trimethylsilylethoxycarbonyl (Teoc) or arylsulfonyl such as 4-methoxy-2,3,6-trimethylphenylsulfonyl (Mtr). Trityl (Trt) is furthermore also known as an amino protective group. Preferred amino protective groups-are Boc, Fmoc and Aloc, furthermore Z, benzyl and acetyl. Boc is particularly preferred.

$R^2$, as described beforehand, is a carboxyl protective group. The expression "carboxyl protective group" is also generally known and relates to groups which are suitable for protecting the hydroxyl group of a carboxylic acid from chemical reactions. Typical groups of this type are the abovementioned unsubstituted or substituted aryl, aralkyl, aroyl or acyl groups, furthermore also alkyl groups, alkyl, aryl or aralkylsilyl groups. The nature and size of the carboxyl protective groups and synonymously therewith of the hydroxyl protective groups is uncritical, as they are removed again after the desired chemical reaction or reaction sequence; groups having 1–20, in particular 1–10, C atoms are preferred. Examples of hydroxyl protective groups are, inter alia, aralkyl groups such as benzyl, 4-methoxybenzyl or 2,4-dimethoxybenzyl, aroyl groups such as benzoyl or p-nitrobenzoyl, acyl groups such as acetyl or pivaloyl, p-toluenesulfonyl, alkyl groups such as methyl or tert-butyl, but also allyl, alkylsilyl groups such as trimethylsilyl (TMS), triisopropylsilyl (TIPS), tert-butyldimethylsilyl (TBS) or triethylsilyl, trimethylsilylethyl or aralkylsilyl groups such as tert-butyldiphenylsilyl (TBDPS). Preferred hydroxyl protective groups are methyl, benzyl, acetyl, tert-butyl or TBS. Methyl and tert-butyl are particularly preferred.

In general, preferred protective groups for the carboxyl group of the aspartic acid side chain are linear or branched alkyl groups, such as methyl, ethyl or tert-butyl, or arylalkyl groups, such as benzyl; in the process according to the invention benzyl.

In general, preferred protective groups for the guanidino group of the arginine side chain are Z, Boc, Mtr or Pmc; in the process according to the invention Pbf.

The liberation of the protective group used in each case is known from the literature (e.g. T. W. Greene, P. G. M. Wuts, Protective Groups in Organic Chemistry, $2^{nd}$ Ed., Wiley, New York 1991 or P. J. Kocienski, Protecting Groups, 1. Ed., Georg Thieme Verlag, Stuttgart—New York, 1994). Use can also be made in this case of variants which are known per se, but not mentioned here in greater detail.

The invention relates to a process, as described beforehand, characterized in that the tripeptide $R^1$-Asp(OBzl)-DPhe-NMeVal-OH, where $R^1$ is an amino protective group, is prepared by linear synthesis by reacting Z-DPhe-OH with H-NMeVal-OMe to give H-DPhe-NMeVal-OMe and then reacting this with an activated $R^1$-Asp(OBzl)-OH derivative and cleaving the methyl ester.

A preferred derivative of $R^1$-Asp(OBzl)-OH is the succinimide $R^1$-Asp(OBzl)-OSu. Further active esters which can be employed are known from the customary literature on peptide synthesis as described beforehand.

The invention furthermore relates to a process, such as described beforehand, characterized in that the dipeptide H-Arg(Pbf)-Gly-$R^2$, where $R^2$ is a carboxyl protective group, is prepared by linear synthesis by reacting Z-Arg(Pbf)-OH with H-Gly-$R^2$ and the protective group Z is removed.

The invention likewise relates to the linear pentapeptides, selected from the group consisting of H-Arg(Pbf)-Gly-Asp(OBzl)-DPhe-NMeVal-OH,
H-Gly-Asp(OBzl)-DPhe-NMeVal-Arg(Pbf)-OH,
H-Asp(OBzl)-DPhe-NMeVal-Arg(Pbf)-Gly-OH,
H-DPhe-NMeVal-Arg(Pbf)-Gly-Asp(OBzl)-OH or
H-NMeVal-Arg(Pbf)-Gly-Asp(OBzl)-DPhe-OH, as intermediates in the synthesis of cyclo(Arg-Gly-Asp-DPhe-NMeVal)., The invention relates to a process for the preparation of the cyclic pentapeptide cyclo(Arg-Gly-Asp-DPhe-NMeVal)

by a) reacting a dipeptide H-Arg(Pbf)-Gly-$R^2$, prepared by linear synthesis of Z-Arg(Pbf)-OH with H-Gly-$R^2$ and subsequent removal of the protective group Z, with b) a tripeptide $R^1$-Asp(OBzl)-DPhe-NMeVal-OH, prepared by linear synthesis of Z-DPhe-OH with H-NMeVal-OMe and removal of the protective group Z to give H-DPhe-NMeVal-OMe and subsequent coupling of this peptide to an active ester of $R^1$-Asp(OBzl)-OH and subsequent removal of the methyl ester, convergently to give the linear pentapeptide $R^1$-Asp(OBzl)-DPhe-NMeVal-Arg(Pbf)-Gly-$R^2$, c) removing the protective groups $R^1$ and $R^2$, d) cyclizing the liberated pentapeptide H-Asp(OBzl)-DPhe-NMeVal-Arg(Pbf)-Gly-OH to give cyclo(Arg(Pbf)-Gly-Asp(OBzl)-DPhe-NMeVal), e) removing the benzyl protective group, f) removing the Pbf protective group with TFA and optionally converting the trifluoroacetate of cyclo(Arg-Gly-Asp-DPhe-NMeVal) produced by the steps a–f) into further physiologically acceptable salts.

Further physiologically acceptable salts are, for example, salts of inorganic acids, such as sulfuric acid, sulfurous acid, dithionic acid, nitric acid, hydrohalic acids such as hydrochloric acid or hydrobromic acid, phosphoric acids such as, for example, orthophosphoric acid, sulfamic acid, furthermore of organic acids, in particular aliphatic, alicyclic, araliphatic, aromatic or heterocyclic mono- or polybasic carboxylic, sulfonic or sulfuric acids, e.g. formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose-1-phosphate, naphthalenemono- and disulfonic acids or laurylsulfuric acid.

Particularly preferred physiologically acceptable salts are the hydrochloride or the internal salts of cyclo(Arg-Gly-Asp-DPhe-NMeVal).

If $R^1$ is Boc and $R^2$ is tert-butyl, these terminal tert-butyl-like protective groups can be cleaved with formic acid without the side-chain protective groups Pbf and Bzl being attacked.

The following examples describe specific embodiments of the individual synthesis steps.

Above and below, all temperatures are indicated in ° C.

EXAMPLE 1

Synthesis of Boc-Asp(OBzl)-DPhe-NMeVal-OH 1. 25.3 ml of trimethylchlorosilane are added dropwise to a solution of 26.5 g of Z-NMeVal-OH in 200 ml of methanol and the mixture is stirred overnight. The reaction mixture is freed from the solvent and the residue is taken up in methyl tert-butyl ether (MTBE) and washed with 5% $Na_2CO_3$ and water. After removal of the solvent, the residue is taken up in methanol and 1N HCl, mixed with water-moist Pd/C (10%) and hydrogenated in a gentle stream of $H_2$. After completion of the reaction, the catalyst is filtered off, the filtrate is freed from the solvent and the residue is recrystallized from ethyl acetate. H-NMeVal-OMe hydrochloride is obtained in a yield of 75%.

2. A solution of 16.1 g of Z-DPhe-OH, 10 g of H-NMeVal-OMe hydrochloride and 10.1 ml of diisopropylethylamine in 100 ml of dichloromethane is cooled to 0–5° and 11.35 g of EDCI are added. The mixture is first stirred-for one hour at 0–5°, then overnight at room temperature. The solvent is removed and the residue is taken up in MTBE and washed with $Na_2CO_3$ (5%), 1N HCl and water and dried. After removal of the solvent, Z-DPhe-NMeVal-OMe is obtained in a yield of 84.5%.

3. 12 g of Z-CPhe-NMeVal-OMe are dissolved in 80 ml of THF and 20 ml of water, mixed with 10 mg of thymolphthalein and treated dropwise with 10M NaOH until a blue colouration of the indicator is obtained. On decolourization of the indicator, the mixture is repeatedly treated drodwise with 10M NaOH. When a decolourization of the indicator is no longer observed, it is adjusted to pH 2 with 10% aqueous KHSO₄ solution, methanol is removed and the product is extracted with MTBE. After drying with Na₂SO₄, the CHA salt is precipitated from the filtrate by addition of 2.9 ml of CHA. Z-DPhe-NMeVal-OHxCHA is obtained in a yield of 90%.

4. 16.4 g of Z-DPhe-NMeVal-OHxCHA (cyclohexylammonium salts) are stirred in 250 ml of MTBE and 100 ml of H₃PO₄ (10%) until everything has dissolved. After removal of the aqueous phase, the organic phase is washed with water and saturated NaCl solution and dried. The solvent is removed and the residue is taken up in 15.2 ml of 2N NaOH and 150 ml of THF and, after addition of the moist catalyst (1 g of Pd/C (10%)), hydrogenated in a gentle stream of H₂. The catalyst is filtered off and the clear solution is treated with 12.1 g of Boc-Asp(OBzl)-OSu and 4.5 ml of triethylamine and stirred overnight at room temperature. After removal of the solvent, the residue is taken up in MTBE and washed with H₃PO₄ (10%), water and saturated NaCl solution. The organic phase is treated with 3.3 ml of CHA. The resulting salt Boc-Asp(OBzl)-DPhe-NMeVal-OHxCHA is filtered off and dried in vacuo. The yield is 93%.

EXAMPLE 2

Synthesis of H-Arg(Pbf)-Gly-OtBu 1. 33.0 g of Z-Arg(Pbf)-OHxCHA are stirred in 300 ml of acetic acid and 300 ml of H₃PO₄ until everything has dissolved. After removal of the aqueous phase, the organic phase is washed with water and saturated NaCl solution and dried. After removal of the solvent, the residue is dissolved in 250 ml of dichloromethane with 8.38 g of H-Gly-OtBuxHCl and cooled to 0°. 17.12 ml of diisopropylethylamine and 16.05 g of TBTU are then added and the mixture is stirred for 60 min at 0° and overnight at room temperature. The solvent is removed and replaced by 250 ml of ethyl acetate. After washing with Na₂CO₃ solution (5%), water and saturated NaCl solution, the solvent is removed. Z-Arg(Pbf)-Gly-OtBu is obtained in a yield of 86%.

2. A solution of 30 g of Z-Arg(Pbf)-Gly-OtBu in 350 ml of THF is mixed with 3 g of water-moist Pd/C (10%) and the Z group is removed by hydrogenation under a gentle stream of H2. The catalyst is then filtered off and the solvent is removed. The residue is taken up in ethyl acetate and treated further as in Example 2.1. H-Arg(Pbf)-Gly-OtBu is obtained in a yield of 86%.

EXAMPLE 3

Synthesis of H-Asp(OBzl)-DPhe-NMeVal-Arg(Pbf)-Gly-OH 1. 1.23 g of Boc-Asp(OBzl)-DPhe-NMeVal-OHxCHA are converted into the free acid in the customary manner and this is dissolved in 12.5 ml of dichloromethane with 0.81 g of H-Arg(Pbf)-Gly-OtBu and 0.22 g of DMAP. The solution is cooled to 0–5° and treated with 0.345 g of EDCI. It is stirred for 2 hours at 0–5° and overnight at room temperature. The solvent is removed, the residue is taken up in MTBE and treated further as in Example 2.1. Boc-Asp(OBzl)-DPhe-NMeVal-Arg(Pbf)-Gly-OtBu is obtained in a yield of 82%.

2. 2.3 g of Boc-Asp(OBzl)-DPhe-NMeVal-Arg(Pbf)-Gly-OtBu are dissolved in 23 ml of 95% formic acid for the removal of the terminal protective groups and concentrated in vacuo after 30 min. The product is triturated with ether, filtered off and dried in vacuo. H-Asp(OBzl)-DPhe-NMeVal-Arg(Pbf)-Gay-OHxHCOOH is obtained in a yield of 95%.

EXAMPLE 4

Synthesis of Cyclo(Arg(Pbf)-Gly-Asp(OBzl)-DPhe-NMeVal)

A solution of 11.9 g of H-Asp(OBzl)-DPhe-NMeVal-Arg(Pbf)-Gly-OHxHCOOH in 60 ml of NMP is added dropwise to a stirred solution of 7.25 g of TBTU and 7.45 ml of N-methylmorpholine in 180 ml of N-methylpyrrolidone. The reaction solution is stirred for 20 hours and then added dropwise to a solution of 47.5 g of NaHCO₃ in 1800 ml of water. The precipitate is filtered and dried in vacuo. Cyclo(Arg(Pbf)-Gly-Asp(OBzl)-DPhe-NMeVal) is obtained in a yield of 73.4%.

EXAMPLE 5

Synthesis of Cyclo(Arg-Gly-Asp-DPhe-NMeVal)

1. A solution of 2 g of cyclo(Arg(Pbf)-Gly-Asp(OBzl)-DPhe-NMeVal) in 26 ml of THF is mixed with 0.5 g of Pd/C (10%). Hydrogen is passed through for 2 hours, the mixture is freed of the catalyst and the solvent is removed in vacuo. The product crystallizes after addition of 32 ml of acetone, and is filtered off and dried. Cyclo(Arg(Pbf)-Gly-Asp-DPhe-NMeVal) is obtained in a yield of 83%.

2. 1.5 g of cylo(Arg(Pbf)-Gly-Asp-DPhe-NMeVal) are dissolved in 15 ml of 95% TFA. After 1 hour, the solution is added dropwise to 150 ml of isopropyl ether and the solid is filtered off and dried. The dried product is dissolved in 30 ml of isopropanol/water 1:2 and treated with ion exchanger III (acetate form; Merck KGaA). The filtered solution is concentrated and freeze-dried. Cyclo(Arg-Gly-Asp-DPhe-NMeVal) is obtained as an internal salt in a yield of 96%.

What is claimed is:

1. A linear pentapeptide selected from the group consisting of

H-Arg(Pbf)-Gly-Asp(OBzl)-DPhe-NMeVal-OH,

H-Gly-Asp(OBzl)-DPhe-NMeVal-Arg(Pbf)-OH,

H-Asp(OBzl)-DPhe-NMeVal-Arg(Pbf)-Gly-OH,

H-DPhe-NMeVal-Arg(Pbf)-Gly-Asp(OBzl)-OH and

M-NMeVal-Arg(Pbf)-Gly-Asp(OBzl)-DPhe-OH, as an intermediate in the synthesis of cyclo(Arg-Gly-Asp-DPhe-NMeVal).

2. A process for the preparation of a cyclic pentapeptide cyclo(Arg-Gly-Asp-DPhe-NMeVal)

comprising cyclizing a linear pentapeptide selected from the group consisting of H-Arg(Pbf)-Gly-Asp(OBzl)-DPhe-NMeVal-OH, H-Gly-Asp(OBzl)-DPhe-NMeVal-Arg(Pbf)-OH, H-Asp(OBzl)-DPhe-NMeVal-Arg(Pbf)-Gly-OH, H-DPhe-NMeVal-Arg(Pbf)-Gly-Asp(OBzl)-OH and H-NMeVal-Arg(Pbf)-Gly-Asp(OBzl)-DPhe-OH, and removing protective groups.

3. A process for the preparation of the cyclic pentapeptide cyclo(Arg-Gly-Asp-DPhe-NMeVal)

according to claim 2, wherein the linear pentapeptide H-Asp(OBzl)-DPhe-NMeVal-Arg(Pbf)-Gly-OH is cyclized.

4. A process according to claim 2, wherein the synthesis of the linear peptide H-Asp(OBzl)-DPhe-NMeVal-Arg (Pbf)-Gly-OH is carried our convergently by fragment condensation of a tripeptide $R^1$-Asp (OBzl)-DPhe-NMeVal-OH, with a dipeptide H-Arg(Pbf)-Gly-$R^2$, where $R^1$ is an amino protective group and where $R^2$ is a carboxyl protective group, and the protective groups $R^1$ and $R^2$ are subsequently removed.

5. A process according to claim 4, wherein the tripeptide $R^1$-Asp(OBzl)-DPhe-NMeVal-OH, where $R^1$ is an amino protective group, is prepared by linear synthesis by reacting Z-DPhe-OH with H-NMeVal-OMe to give H-DPhe-NMeVal-OMe, which is then reacted with an activated $R^1$-Asp(OBzl)-OH derivative and the methyl ester is cleaved.

6. A process according to claim 4, wherein the dipeptide H-Arg(Pbf)-Gly-$R^2$, where $R^2$ is a carboxyl protective group, is prepared by linear synthesis by reacting Z-Arg(Pbf)-OH with H-Gly-$R^2$ and removing the protective group Z.

7. The process according to claim 2, wherein said cyclic pentapeptide is converted into a physiologically acceptable salt.

8. A process for the preparation of the cyclic pentapeptide cyclo(Arg-Gly-Asp-DPhe-NMeVal) comprising
   a) reacting a dipeptide H-Arg(Pbf)-Gly-$R^2$ with a tripeptide $R^1$-Asp(OBzl)-DPhe-NMeVal-OH to yield the linear pentapeptide $R^1$-Asp(OBzl)-DPhe-NMeVal-Arg(Pbf)-Gly-$R^2$, wherein $R^1$ is an amino protective group and $R^2$ is a carboxyl protective group,
   b) removing the protective $R^1$ and $R^2$ groups,
   c) cyclizing the liberated pentapeptide H-Asp(OBzl)-DPhe-NMeVa-Arg(Pbf)-Gly-OH to yield cyclo(Arg(Pbf)-Gly-Asp(OBzl)-DPhe-NMeVal), and
   d) removing the Bzl and Pbf protective groups.

9. The process according to claim 8, wherein the dipeptide H-Arg(Pbf)-Gly-$R^2$ is prepared by linear synthesis of Z-Arg(Pbf)-OH with H-Gly-$R^2$ and the subsequent removal of the protective group Z.

10. The process according to claim 8, wherein the tripeptide $R^1$-Asp(OBzl)-DPhe-NMeVal-OH is prepared by
   i) linearly synthesizing Z-DPhe-OH with H-NMeVal-OMe,
   ii) removing the protective group Z to yield H-DPhe-NMeVal-OMe,
   iii) coupling the peptide from ii) to an active ester of $R^1$-Asp(OBzl)-OH, and
   iv) removing the methyl ester.

11. The process of claim 8, wherein the Pbf protective group is removed with TFA.

12. The process according to claim 8 further comprising converting the trifluoracetate of cyclo(Arg-Gly-Asp-DPhe-NMeVal) into a physiologically acceptable salt.

13. The process according to claim 12, wherein the physiologically acceptable salt is a hydrochloride or an internal salt of cyclo(Arg-Gly-Asp-DPhe-NMeVal).

\* \* \* \* \*